(12) United States Patent
Rosso

(10) Patent No.: US 6,432,114 B1
(45) Date of Patent: Aug. 13, 2002

(54) DEVICE FOR MAKING HYDRO-MICROABRASIONS ON HUMAN TISSUE

(75) Inventor: Luciano Rosso, Caselette (IT)

(73) Assignee: L.I.C.A. S.r.L., Turin (IT)

(*) Notice: Subject to any disclaimer, the term of this patent is extended or adjusted under 35 U.S.C. 154(b) by 0 days.

(21) Appl. No.: 09/594,609

(22) Filed: Jun. 15, 2000

(30) Foreign Application Priority Data

Jun. 16, 1999 (IT) .......................... TO99A0522

(51) Int. Cl.[7] ............................... A61M 1/00
(52) U.S. Cl. ....................................... 606/131
(58) Field of Search ................ 606/131, 132, 606/159; 604/289, 290, 313, 315

(56) References Cited

U.S. PATENT DOCUMENTS

| | | | |
|---|---|---|---|
| 4,595,365 A | | 6/1986 | Edel et al. |
| 5,037,432 A | * | 8/1991 | Molinari ............... 606/131 |
| 5,547,376 A | | 8/1996 | Harrel |
| 5,971,999 A | * | 10/1999 | Naldoni ............... 606/131 |
| 6,024,733 A | * | 2/2000 | Eggers et al. ......... 604/500 |
| 6,039,745 A | * | 3/2000 | Di Fiore et al. ....... 606/131 |
| 6,080,165 A | * | 6/2000 | DeJacma ............. 606/131 |
| 6,162,232 A | * | 12/2000 | Shadduck ............. 606/131 |
| 6,238,275 B1 | * | 5/2001 | Metcalf ................ 451/87 |
| 6,241,739 B1 | * | 6/2001 | Waldron ............. 606/131 |

FOREIGN PATENT DOCUMENTS

| | | |
|---|---|---|
| EP | 0 143 617 A2 | 6/1985 |
| EP | 0 324 448 A1 | 7/1989 |

\* cited by examiner

*Primary Examiner*—Jeffrey A. Smith
*Assistant Examiner*—Michael B. Priddy
(74) *Attorney, Agent, or Firm*—Sughrue Mion, PLLC

(57) ABSTRACT

A device for making micro-abrasions on human tissue including a handle having an inlet passage and an outlet passage which communicate with an aperture provided in the handle and intended to be positioned on the surface to be treated, and supply means for the metered supply of reducing substances in a pneumatic carrier from a supply container connected to the inlet passage, to the aperture of the handle. The device is further arranged for selective and controlled supply of a liquid to the aperure of the handle.

22 Claims, 2 Drawing Sheets

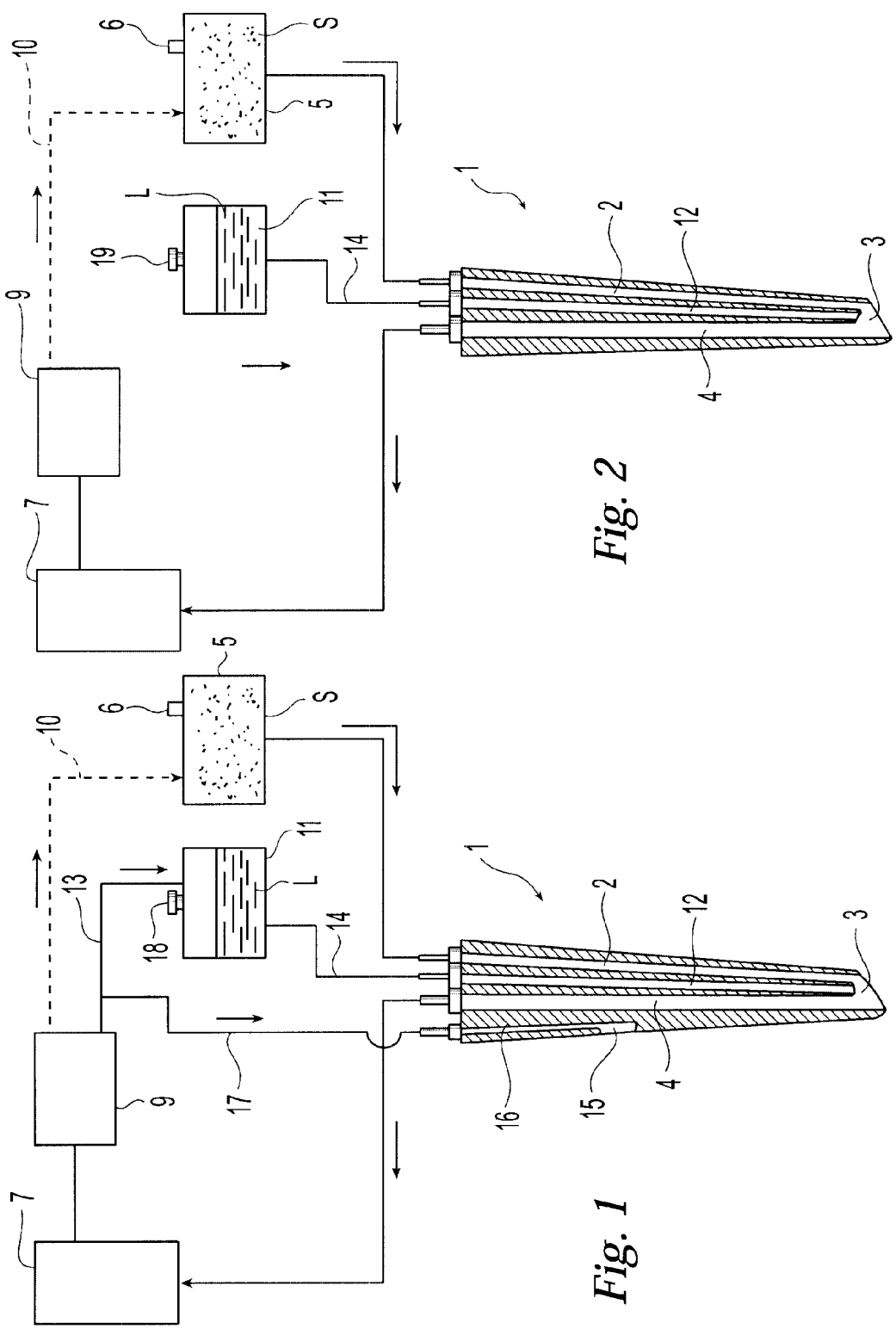

DEVICE FOR MAKING HYDRO-MICROABRASIONS ON HUMAN TISSUE

BACKGROUND OF THE INVENTION

The present invention is to generally related to devices for making microabrasions on human tissue.

Presently known devices for human tissue microabrasion employ peculiar reducing substances in a pneumatic carrier. These known devices comprise a handle having an inlet passage and an outlet passage which communicate with an aperture provided in the handle and intended to be positioned on the surface to be treated, and supply means for the metered supply of reducing substances in a pneumatic carrier from a supply container of said reducing substances, connected to the inlet passage, to the aperture of the handle.

Such known devices are disclosed and illustrated in Italian patents IT-B-1184922 and IT-B-1218945 (corresponding to European patent EP-B2-0324448). Moreover, apparatuses reducing into practice the solutions according to the above mentioned two documents have been since long produced and marketed with success world-wide in connection with mainly aesthetical treatments, such as for instance for treating scars and stretch marks and even for partially or totally removing tattoos, and also in connection with medical treatments. The reducing substances employed during microabrasion treatments performed by these apparatuses are normally consisting of corundum micro-crystals, which are delivered to the aperture of the handle according to two different functional principles: in one case (corresponding to the apparatus discloses in Italian patent IT-B-1184922) the pneumatic carrier flow is under overpressure, while in the other case (corresponding to the apparatus according to the Italian patent IT-B-1218945) the flow is under vacuum. In the first case the pneumatic carrier flow is generated by an air compressor directly or indirectly (through an ejector system) connected to the supply container of the reducing substances, and a small low-power suction pump is provided, which is connected to the outlet passage of the handle for drawing the reducing substances along with the removed fragments of the human tissue. The action of the reducing substances onto the treated surface is anyhow operated under overpressure.

In the second case of the pneumatic flow of the reducing substances under vacuum is provided by a suction pump connected to a collecting container of the exhaust reducing substances and of the removed tissue particles, which is in turn connected to the outlet passage of the handle and then, through the inlet passage thereof, with the supply container of the reducing substances, whereby, in operation, the flow thereof subjected to the force which is necessary to perform microabrasion of the human tissue, takes place only as a result of the closure of the aperture of the handle against the surface to be treated. The supply container of the reducing substances is provided with an air-intake passage, and the air inlet through this intake passage can be adjusted for instance by changing the cross section of the air-intake passage.

Alternatively, in some apparatus of this type an air pressure source (normally a small low-power air compressor) can also be provided, which is connected to the supply container of the reducing substances so as to super charge air thereinto, and providing a swirling effect of the reducing substances within the supply container by virtue of which the amount of these reducing substances delivered to the handle is increased and, as a consequence, the abrasive action is enhanced. The pneumatic carrier flow of the reducing substances, i.e. the working force provided by the apparatus, is anyway even in this case always and solely under vacuum.

SUMMARY OF THE INVENTION

The general object of the present invention is to improve the above disclosed devices for making microabrasions on the human tissue.

A particular object of the present invention is to provide a device for making microabrasions on human tissue of the type referenced at the beginning, which is designed to enhance efficiency of the abrasive treatment and the related effects.

This object is achieved mainly by the fact that the human tissue microabrasion device according to the invention is characterised in that it is arranged for selective and controlled supply of a liquid onto the surface to be treated.

In general terms this liquid itself may provide the fluid carrier of the reducing substances towards the aperture of the handle, thus replacing the pneumatic flow, or can be combined with such a pneumatic flow either upstream the aperture of the handle or downstream the handle itself, or as well in correspondence of the aperture thereof intended to be positioned on the surface to be treated.

In the latter case the handle may include a second inlet passage for the selective supply of the liquid to said aperture of the handle.

According to a further alternative embodiment the liquid itself may constitute exclusively (i.e. without the presence of a pneumatic stream) the carrier of the abrasive substances, which in such a case shall consist not of a reducing powder but instead of reducing liquids. Accordingly the liquid itself shall autonomously provide an hydro-microabrasion of the human tissue.

This liquid may simply be water, possibly at a very low temperature or in a steam state, even mixed together with one or more substances selected within the following classes: anaesthetic, hemostatic and coagulative, nutritious, cicatrizing, slightly corrosive, regenerative, refreshing, lenitive and calmative, moistening, lubricating, hydrating and the like. In case the device be mainly intended for removing tattoos, stains and generally cutaneous defects, the liquid shall conveniently consist of a physiological solution possibly enriched with some ingredients such as sodium and derivatives thereof.

The invention contemplates several specific embodiment wherein, while the flow of the reducing substances in a pneumatic carrier is either under overpressure or under vacuum, respectively, the liquid may be supplied to the aperture of the handle according to alternative combinations either under overpressure or under vacuum.

BRIEF DESCRIPTION OF THE DRAWINGS

These specific embodiments will now be disclosed in detail with reference to annexed drawings, given purely by way of non limiting example, in which:

FIG. 1 diagrammatically shows a device for making microabrasions on human tissue according to a first particular embodiment of the invention, FIG. 2 is a view similar FIG. 1 of a first alternative embodiment of the device according to the invention.

DETAILED DESCRIPTION OF THE INVENTION

Figure 3:
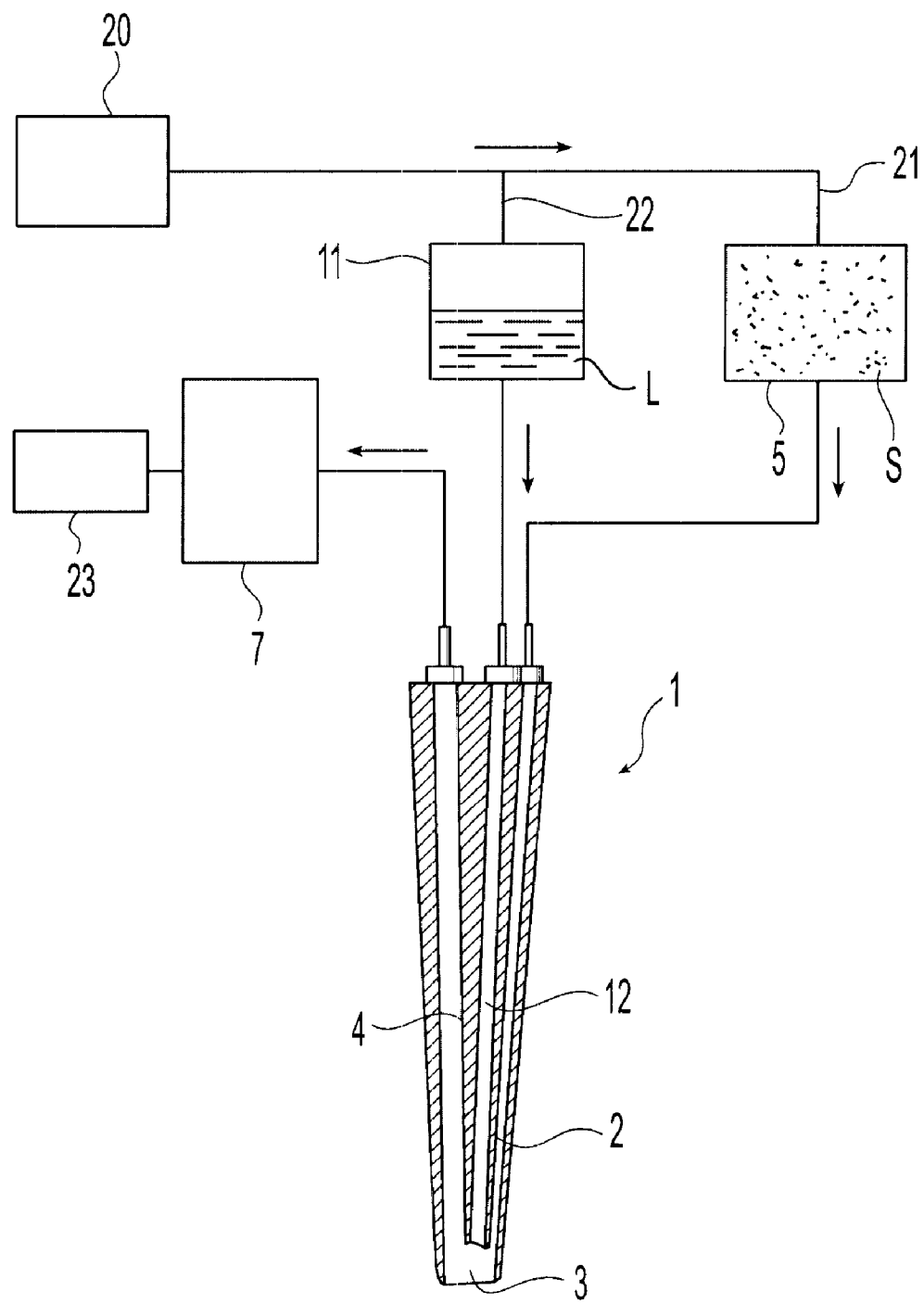
FIG. 3 shows a second alternative embodiment of the device.

The embodiment diagrammatically depicted in FIG. 1 corresponds to the case of the functional principle of the known devices wherein the flow of human tissue microabrasion is pneumatic and under vacuum, i.e. is corresponding—as far as the microabrasion action in a pneumatic carrier is concerned—to the one disclosed in Italian patent IT-B-1218945 already mentioned. The device according to this embodiment comprises a handle 1, consisting of a body designed to be grasped and handled by an operator, possibly fully or in part disposable. This handle 1, whose shape and arrangement (also including a slight inclination thereof) is shown in the drawings by way of mere example, is provided with an inlet passage 2 ending in correspondence of an aperture 3 from which an outlet passage 4 is departing. The size of the aperture 3 in the drawing is intentionally exaggerated as compared with the size of the whole handle 1, and also the arrangement of the inlet passage 2 and of the outlet passage 2 is purely diagrammatic and is simply provided by way of example. These passages may actually be also conveniently arranged coaxially to each other.

In a way known per se by Italian patent IT-B-1218945 already mentioned, the inlet passage 2 is connected to a container 5, possibly disposable, containing an amount of reducing substances, normally micro-crystals of corundum. The container 5, which in the following will be designated as supply container, communicates to the atmosphere through an air-intake passage diagrammatically shown as 6, through which the intake air flow can be adjusted for instance by changing the section of the passage 6 even by means of a valve system not shown in the drawing.

Also in a way known per se, the outlet passage 4 is communicating with a collecting container 7 which in turn is connected to the inlet of a suction pump 9. The outlet pressure side of the suction pump 9 may possibly be connected, via a supercharging line 10, with the supply container 5, through the air-intake passage 6 or (as in the case of the shown example) through one or even more separate ports.

In operation, the suction pump 9 constitutes the one and sole feeding means for the supply in a metered way (through a manually operated conventional regulation unit, not shown in the drawings, associated to the suction pump 9) of the reducing substances S contained within the supply container 5 towards the area to be treated onto which the aperture 3 of the handle 1 is applied. In fact, as a result of the closure of the aperture 3 against the human tissue, the reducing substances S are drawn from the supply container 5 into the inlet passage 2 and then towards the aperture 3, thus performing the human tissue microabrasion action, and them through the outlet passage 4 to the collecting container 7 the interior of which is maintained under vacuum by the vacuum pump 9. The pneumatic flow of the reducing substances S towards the aperture 3 is interrupted as soon as the latter is separated from the area under treatment, since in that case the suction pump 9 will be placed in direct communication with the atmosphere through the aperture 3.

The amount of the abrasive action performed by the reducing substances S can be adjusted to the needs either by means of the regulation unit associated to the suction pump 9, or by adjusting—as explained—the air inlet through the intake passage 6, or by controlling delivery of the air under pressure, if any, from the outlet side of the suction pump 9 into the supply container 5 through the supercharging line 10. It is to be pointed out that this supercharging line 10 may be connected, instead than to the outlet side of the suction pump 9, to the delivery side of a suitable air compressor having a limited power.

Air supercharging into the supply container 5 provides an increase of the amount of reducing substances S supplied under vacuum to the inlet passage 2 and then to the aperture 3, thus making the microabrasion action more strong.

Anyway, independently of the presence of the supercharging line 10, according to the above-disclosed arrangement the human tissue abrasion treatment is carried out by a pneumatic flow under vacuum of the reducing substances S.

According to the primary feature of the invention, the microabrasion device is further provided with a system for the selective and controlled supply of a liquid L to the aperture 3 of the handle 1 either in an independent or a combined way with respect to delivery of the pneumatic flow of the reducing substances S to the aperture 3.

To such effect the handle 1 is provided with a second inlet passage 12 connected to a vessel 11 containing liquid L whose characteristic shall be specified in the following.

Supply of the liquid L from the vessel 11 to the aperture 3 of the handle 1 can be carried out either by overpressure or by vacuum. In the former case, corresponding to the embodiment which is now been disclosed with reference to FIG. 1, the vessel 11 is connected through a line 13 (directly as in the shown example, or indirectly through an ejector system) to an overpressure source, and through a line 14 with the second inlet passage 12. This overpressure source may consist of an hydraulic pump or more simply by an air compressor, for instance the same one (whenever provided for) which is provided for supercharging air to the supply container 5 of the reducing substances S. Still more conveniently the overpressure can be provided by the outlet side of the vacuum pump 9 itself, connected to the line 13 through a check valve unit of a conventional type, not shown in the drawing. This check valve unit can be alternatively constituted, in a unique way, by a vent hole 15 formed on the handle 1 itself and communicating with a third inlet passage 16 of the handle 1 which is in turn connected through a duct 17 with the line 13 upstream of the vessel 11 for the liquid L. The vent hole 15 can be closed for instance manually by the operator: in operation, if the vent hole 15 remains open, the air under pressure fed by the outlet side of the vacuum pump 9 (or by the air micro-compressor, whenever provided) directly exits to the atmosphere through the line 17 and the third inlet passage 16. In this case no forced supply of liquid L from the vessel 11 to the aperture 3 of the handle 1 takes place. If instead the vent hole 15 is closed by the operator, the air under pressure delivered into the line 13 pressurizes the vessel 11, whereby the liquid L therein is delivered under pressure to the second inlet passage 12 and then, through the aperture 3, onto the area under treatment.

Naturally, different systems for controlling supply under pressure of the liquid can be envisaged, not only in a combined way but even independently with respect to the supply of the reducing substances S from the supply container 5 to the aperture 3 of the handle 1. For instance, the liquid under pressure may be delivered onto the surface to be treated before or after the pneumatic flow of the reducing substances takes place, so as to perform a tissue iperemization action. However it has been found that the combination of the liquid flow along with the pneumatic flow surprisingly improves in general the abrasive action performed by the reducing substances.

The amount of the overpressure under which the liquid L is fed from the vessel 11 to the aperture 3 of the handle 1 can be widely varied, and also adjusted by means of expedients within the knowledge of the expert.

The vessel 11 can consist, as already pointed out, of a disposable bottle or—as in the case of the shown example—of a refillable container having a removable plug 18. The liquid L contained therein may simply consist of water, and in that case the jet under pressure thereof through the aperture 3 of the handle 1 will perform iperemization of the tissue area under treatment either prior to and/or during and/or following abrasion performed by the pneumatic flow of reducing substances. The liquid may also be delivered in a steam status, so as to provide an efficient dilatation effect of the skin pores under treatment, and accordingly the vessel 11 shall be equipped with a proper boiler, not shown in the drawings, for instance of the electrical-resistor type, even providing instantaneous steam generation. As an alternative the vessel 11 can be operatively equipped with a refrigerating device, even of the instantaneous type, whereby the liquid supplied to the aperture 3 on the handle 1 shall be cooled down even to a very low temperature, with the effect of reducing the sensitiveness of the human tissue to the action of the reducing substances S.

The liquid L contained within the vessel 11 may conveniently consist of a mixture of one or more of the substances selected in the following classes:

anaesthetic, hemostatic and coagulative, nutritious (collagen, elastins), cicatrizing (phytostimulins, biostimulins), slightly corrosive (glycolic acid, hydrochloric acid and the like), regenerative, refreshing, lenitive and calmative, moistening, lubricating, hydrating, etc.

Among the substances presently considered particularly useful for mixing thereof together with water or other treatment liquid, sodium chloride is included, whose efficacy revealed particularly relevant whenever the microabrasion device is employed to remove tattoos from the skin.

Obviously the effect of the liquid flow applied onto the area being treated shall correspond to the intrinsic characteristic of those substances, which may also be combined and mixed together variously.

After having operated on the human tissue treatment area, the exhaust liquid along with the exhaust reducing substances are captured within the collecting container 7 and subsequently evacuated.

It is to be pointed out that with the above-disclosed arrangement the liquid L coming from the vessel 11 and the reducing substances S coming from the supply container 5 are mixed together in correspondence of the aperture 3 of the handle 1: as an alternative, and as already explained in the above, mixing may even take place upstream of the aperture 3, and even upstream of the handle 1: in such a case the handle 1 shall be designed according to a conventional arrangement, with only one inlet passage for the supply of the reducing substances S—liquid L mixture to the aperture 3.

A different embodiment can also be envisaged wherein the flow of liquid itself constitutes the fluid carrier displacing the reducing substances, for instance by means of an ejector system, thus replacing the pneumatic carrier.

In the embodiment specifically disclosed in the above with reference to FIG. 1, the supply of the reducing substances S and the supply of the liquid L to the aperture 3 of the handle 1 are performed, as explained, respectively under vacuum and under overpressure.

The invention contemplates alternative embodiments in which the reducing substances S and the liquid L can be supplied both under vacuum, or both under overpressure, or the former under overpressure and the latter under vacuum.

The first alternative embodiment is depicted in FIG. 2, wherein parts identical or similar to those already previously disclosed are indicated by the same reference numerals. According to this variant the vessel 11 for the liquid L is communicating to the atmosphere through an air-intake passage 19, and the flow of the liquid L towards the aperture 3 of the handle 1 is carried out by the vacuum applied within the collecting container 7 by the vacuum pump 9. Naturally valve and control systems (not shown in the drawings since generally within the skill of the expert) shall be provided to open, close and adjust the flow of liquid L towards the second inlet passage 12 of the handle 1.

In the case of the variant shown in FIG. 3, wherein parts identical or similar to those already previously disclosed are also designated by the same reference numerals, both the reducing substances S within the supply container 5 and the liquid L within the vessel 11 are fed under overpressure to the aperture 3 of the handle 1. In this case a powerful air compressor 20 is provided, whose delivery side is connected in parallel, either directly as in the case of the shown example or through respective ejector systems, via respective lines 21, 22 to the supply container 5 and/or the vessel 11 which in turn are connected, as in the previously disclosed embodiments, with the first inlet passage 2 and with the second inlet passage 12, respectively, of the handle 1.

The collecting container 7 connected to the outlet passage 4 of the handle 1 is normally connected to a suction pump 23 having a low power, designed to for draw away the exhaust reducing substances and liquid. This variant corresponds conceptually, as far as the pneumatic flow under overpressure of the reducing substances is concerned, to what is disclosed and illustrated in Italian patent IT-B-1184922 already previously mentioned.

While in the examples disclosed in the above with reference to the drawings the circulation of the liquid is conveniently carried out substantially by means of the same functional components providing circulation of the pneumatic carrier, it is to be pointed out that alternatively the liquid circuit may be instead autonomous and independent.

It will be apparent from the above disclosure that the device for making microabrasion on human tissue according to the invention affords, as compared with conventional apparatuses, the advantage of adding to the abrasive action also additional effects deriving from the characteristics of the liquid which can be selectively supplied through the handle to the area under treatment. Experimental texts which are presently being carried out by the applicant provide evidence of the fact that the functional efficiency of the microabrasion device is thus surprisingly enhanced.

Equally surprisingly it is been ascertained that, if the liquid flow is mixed with the reducing substances upstream of the handle so as to avoid the provision of the pneumatic carrier for transporting the reducing substances, abrasive efficiency is not only acceptable but, in certain instances, quite increased particularly whenever the liquid employed comprises corrosive substances.

Naturally the details of construction and the embodiments may be widely varied with respect to what has been disclosed and illustrated by way of example, without thereby departing from the scope of the present invention such as defined in the appended claims.

Thus, again by way of example, a further alternative solution—not shown in the drawings—is comprised within the scope of the invention, wherein the liquid (properly selected among the mixtures of substances listed in the above) completely replaces the solid abrasive substances. In other words the liquid itself may constitute in an exclusive way (i.e. without the presence of a pneumatic flow) the carrier of the abrasive substances, which in this case shall be in fact constituted not by a powder but by reducing liquids, adapted to autonomously provide an hydro-microabrasion action of the human tissue.

What is claimed is:

1. An apparatus for supplying an abrasive treatment flow for making microabrasions on an area of human tissue to be treated, comprising first supply means for the metered supply of reducing substances in a fluid carrier onto the area to be treated and a second supply means for the selective and controlled supply of a liquid to said area to be treated, wherein said fluid carrier of said reducing substances is pneumatic and wherein said reducing substances and said liquid are both supplied under vacuum.

2. Apparatus according to claim 1, further comprising means for heating said liquid.

3. Apparatus according to claim 1, further comprising means for refrigerating said liquid.

4. Apparatus according to claim 1, wherein said liquid is essentially water.

5. Apparatus according to claim 1, wherein said liquid consists of a mixture of water with one or more of the substances selected in the following classes:

anaesthetic; hemostatic and coagulative; nutritious; cicatrizing; corrosive; regenerative; refreshing; lenitive and calmative; moistening; lubricating and hydrating.

6. Apparatus according to claim 1, wherein said liquid includes a physiological solution enriched with ingredients such as sodium and derivatives thereof.

7. Apparatus according to claim 1 further comprising mixing means for mixing said liquid together with said reducing substances including a handle having first and second inlet passages connected to said first and second supply means respectively and an outlet passage communicating with an aperture provided on said handle and intended to be positioned onto the surface to be treated.

8. A device for making microabrasions on human tissue including a handle having first and second inlet passages and an outlet passage which communicate with an aperture provided in the handle and intended to be positioned on the surface to be treated, supply means for the metered supply of reducing substances connected to said first inlet passage of said handle for the metered supply of reducing substances in a pneumatic carrier to said aperture of said handle and delivery means connected to said second inlet passage for delivering a liquid to said aperture in said handle wherein said supply means comprises a vacuum source connected to said outlet passage of said handle for drawing under vacuum said reducing substances from said supply container toward said aperture of said handle through said first inlet passage as well as for drawing under vacuum said liquid from said vessel towards said aperture of said handle through said second inlet passage upon closure of said aperture against the surface to be treated.

9. Device according to claim 8, wherein heating means are provided for heating said liquid.

10. Device according to claim 8, wherein refrigerating means are provided for cooling said liquid.

11. Device according to claim 8, wherein said liquid is water.

12. Device according to claim 11, wherein said liquid consists of a mixture of water with one or more of the substances selected in the following classes; anaesthetic; hemostatic and coagulative; nutritious; cicatrizing; corrosive; regenerative; refreshing; lenitive and calmative; moistening; lubricating and hydrating.

13. Device according to claim 8, wherein said liquid includes a physiological solution enriched with ingredients such as sodium and derivatives thereof.

14. A device for making microabrasions on human tissue including a handle having first and second inlet passages and an oulet passage which communicate with an aperture provided in the handle and intended to be positioned on the surface to be treated, a supply means for supplying a metered supply of said reducing substances in an pneumatic carrier to said first inlet passage and delivery means for the selective and controlled supply of a liquid to said second inlet passage, wherein said supply means comprises a vacuum source connected to said outlet passage of said handle for drawing under vacuum said reducing substances from said supply means towards said aperture of said handle through said first inlet passage upon closure of said aperture against the surface to be treated, said vacuum source having an air delivery side connected to said delivery means for said liquid for delivering under overpressure said liquid to said aperture through said second inlet passage of said handle.

15. A device according to claim 14, wherein said handle has a third inlet passage connected with said air delivery side of said vacuum source and valve means for communicating said third inlet passage with the atmosphere.

16. A device according to claim 15, wherein said valve means is comprised of a vent hole provided on said handle and designed to be closed manually.

17. A device for making microabrasions on human tissue including a handle having first and second inlet passages and an outlet passage which communicate with an aperture provided in the handle and intended to be positioned on the surface to be treated, supply means for the metered supply of reducing substances into said aperture of said handle through said first inlet passage and delivery means for selectively supplying a liquid to said aperture through said second inlet passage, further comprising a suction source connected to said outlet passage of said handle for drawing under vacuum said liquid from said delivery means towards said aperture of said handle through said second inlet passage upon closure of said aperture against the surface to be treated, said vacuum source having an air delivery side connected to said supply means for said reducing said substances for delivering under over pressure said reducing substances to said aperture through said first inlet passage.

18. Device according to claim 17, wherein heating means are provided for heating said liquid.

19. Device according to claim 17, wherein refrigerating means are provided said liquid.

20. Device according to claim 17, wherein said liquid is water.

21. Device according to claim 17, wherein said liquid consists of a mixture of water with one or more of the substances selected in the following classes; anaesthetic; hemostatic and coagulative; nutritious; cicatrizing; corrosive; regenerative; refreshing; lenitive and calmative; moistening; lubricating; hydrating and the like.

22. Device according to claim 17, wherein said liquid includes a physiological solution enriched with ingredients such as sodium and derivatives thereof.

* * * * *